(12) United States Patent
Simen et al.

(10) Patent No.: US 8,344,123 B2
(45) Date of Patent: Jan. 1, 2013

(54) SYSTEM AND METHOD FOR DETECTION OF HIV TROPISM VARIANTS

(75) Inventors: Birgitte Binderup Simen, Orange, CT (US); Elizabeth Patricia St. John, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 0 days.

(21) Appl. No.: 12/970,036

(22) Filed: Dec. 16, 2010

(65) Prior Publication Data

US 2011/0165556 A1    Jul. 7, 2011

Related U.S. Application Data

(62) Division of application No. 12/456,528, filed on Jun. 17, 2009, now Pat. No. 7,888,034.

(60) Provisional application No. 61/077,356, filed on Jul. 1, 2008.

(51) Int. Cl.
*C07H 21/04* (2006.01)
*C12Q 1/68* (2006.01)
*C12P 19/34* (2006.01)

(52) U.S. Cl. ............ 536/24.33; 435/6.12; 435/91.2

(58) Field of Classification Search .............. None
See application file for complete search history.

(56) References Cited

U.S. PATENT DOCUMENTS

| | | | |
|---|---|---|---|
| 6,210,891 B1 | 4/2001 | Nyren et al. | 435/6 |
| 6,258,568 B1 | 7/2001 | Nyren | 435/91.1 |
| 6,274,320 B1 | 8/2001 | Rothberg et al. | 435/6 |
| 6,727,060 B2 * | 4/2004 | Philpott et al. | 435/5 |
| 6,828,100 B1 | 12/2004 | Ronaghi | 435/6 |
| 7,206,699 B2 | 4/2007 | Larder et al. | 702/19 |
| 7,211,390 B2 | 5/2007 | Rothberg et al. | 435/6 |
| 7,323,305 B2 | 1/2008 | Leamon et al. | 435/6 |
| 7,575,865 B2 | 8/2009 | Leamon et al. | 435/6 |
| 7,601,499 B2 | 10/2009 | Berka et al. | 435/6 |
| 2004/0185484 A1 | 9/2004 | Costa et al. | 506/14 |
| 2004/0191269 A1* | 9/2004 | Lu et al. | 424/188.1 |
| 2005/0042648 A1 | 2/2005 | Griffiths et al. | 435/6 |
| 2005/0064460 A1 | 3/2005 | Holliger et al. | 435/6 |
| 2005/0079510 A1 | 4/2005 | Berka et al. | 506/16 |
| 2005/0227264 A1 | 10/2005 | Nobile et al. | 435/6 |
| 2006/0228721 A1 | 10/2006 | Leamon et al. | 435/6 |
| 2006/0228722 A1 | 10/2006 | Kim et al. | 435/6 |
| 2009/0053724 A1 | 2/2009 | Roth et al. | 435/6 |
| 2009/0105959 A1 | 4/2009 | Braverman et al. | 702/19 |
| 2009/0203086 A1 | 8/2009 | Chen et al. | 435/91.5 |
| 2009/0233291 A1 | 9/2009 | Chen et al. | 435/6 |

FOREIGN PATENT DOCUMENTS

| | | |
|---|---|---|
| WO | WO 2007/088201 | 8/2007 |
| WO | WO 2008/062385 | 5/2008 |
| WO | WO 2008/115427 | 9/2008 |
| WO | WO 2010/000427 | 1/2010 |

OTHER PUBLICATIONS

Lowe et al., A computer program for selection of oligonucleotide primers for polymerase chain reactions. Nucleic Acids Research, vol. 18, No. 7, pp. 1757-1761, 1990.*
Lowe et al. ((1990), Nucleic Acids Research, 18:1757-1761.
U.S. Appl. No. 12/380,139, filed Feb. 23, 2009, Simons et al.
U.S. Appl. No. 61/118,815, filed Dec. 1, 2008, Simen et al.
Ahmadian et al. (2000), Analytical Biochemistry, 280:103-110.
Altschul et al. (1990), Journal Molecular Biology, 215:403-410.
Archer et al. (2009), AIDS, 23:1209-1218.
Jensen et al. (2003), AIDS, 5:104-112.
Jensen et al. (2003), Journal of Virology, 77:13376-13388.
Jensen et al. (2006), Journal of Virology, 80:4698-4704.
Lewis, et al. (2007), 14th Conference on Retroviruses and Opportunistic Infections, Abstract 680.
Merrifield (1964), Biochemistry, 3:1385-1390.
Nelson et al. (1997), Journal of Virology, 71:8750-8758.
Poveda et al. (2006), AIDS, 20:1359-1367.
Rickert et al. (2002), BioTechniques, 32:592-603.
Smith et al. (1981), Journal Molecular Biology, 147:195-197.
Thompson et al. (1997), Nucleic Acids Research, 25:4876-4882.
Wang et al. (2007), Genome Research, 17:1195-1201.
Westby et al. (2006), Journal of Virology, 80:4909-4920.
International Search Report for PCT/EP2009/004672, mailed Oct. 8, 2009.

* cited by examiner

*Primary Examiner* — Prabha Chunduru
(74) *Attorney, Agent, or Firm* — Mintz Levin Cohn Ferris Glovsky and Popeo, P.C.; Ivor R. Elrifi

(57) ABSTRACT

An embodiment of a method for detecting low frequency occurrence of one or more HIV sequence variants associated with drug resistance is described that comprises the steps of: generating cDNA species from each RNA molecule in an HIV sample population; amplifying at least one first amplicon from the cDNA species, wherein each first amplicon comprises a plurality of amplified copies and is amplified with a pair of nucleic acid primers that define a locus of the first amplicon; clonally amplifying the amplified copies of the first amplicons to produce a plurality of second amplicons wherein a plurality of the second amplicons comprise an immobilized population of substantially identical copies from one of the amplified copies of first amplicons; determining a nucleic acid sequence composition of the substantially identical copies from at least 100 of the immobilized populations in parallel on a single substrate; and detecting one or more sequence variants that occur at a frequency of 5% or less in the nucleic acid sequence composition of the at least 100 immobilized populations; and correlating the detected sequence variants with variation associated with HIV tropism.

8 Claims, 5 Drawing Sheets

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial
<220> FEATURE:
<223> OTHER INFORMATION: Oligonucleotide Primer

<400> SEQUENCE: 1
tcagcacagt acartgyaca catgg                                         25

<210> SEQ ID NO 2
<211> LENGTH: 24
<212> TYPE: DNA
<213> ORGANISM: Artificial
<220> FEATURE:
<223> OTHER INFORMATION: Oligonucleotide primer

<400> SEQUENCE: 2
cattacaatt tctrggtcyc ctcc                                          24

<210> SEQ ID NO 3
<211> LENGTH: 25
<212> TYPE: DNA
<213> ORGANISM: Artificial
<220> FEATURE:
<223> OTHER INFORMATION: Oligonucleotide primer

<400> SEQUENCE: 3
caactcaact rctgttaaat ggyag                                         25

<210> SEQ ID NO 4
<211> LENGTH: 24
<212> TYPE: DNA
<213> ORGANISM: Artificial
<220> FEATURE:
<223> OTHER INFORMATION: Oligonucleotide primer

<400> SEQUENCE: 4
tgttgtatta cagtagaara aytc                                          24

<210> SEQ ID NO 5
<211> LENGTH: 50
<212> TYPE: DNA
<213> ORGANISM: Artificial
<220> FEATURE:
<223> OTHER INFORMATION: Oligonucleotide primer

<400> SEQUENCE: 5
cgtatcgcct ccctcgcgcc atcagtcagc acagtacart gyacacatgg              50
```

```
<210> SEQ ID NO 6
<211> LENGTH: 49
<212> TYPE: DNA
<213> ORGANISM: Artificial
<220> FEATURE:
<223> OTHER INFORMATION: Oligonucleotide primer

<400> SEQUENCE: 6
ctatgcgcct tgccagcccg ctcagcatta caatttctrg gtcycctcc          49

<210> SEQ ID NO 7
<211> LENGTH: 50
<212> TYPE: DNA
<213> ORGANISM: Artificial
<220> FEATURE:
<223> OTHER INFORMATION: Oligonucleotide primer

<400> SEQUENCE: 7
cgtatcgcct ccctcgcgcc atcagcaact caactrctgt taaatggyag          50

<210> SEQ ID NO 8
<211> LENGTH: 54
<212> TYPE: DNA
<213> ORGANISM: Artificial
<220> FEATURE:
<223> OTHER INFORMATION: Oligonucleotide

<400> SEQUENCE: 8
aggtagaaaa ttaagagaac aatttaataa tagaacaata gtctttaatc aatc     54

<210> SEQ ID NO 9
<211> LENGTH: 54
<212> TYPE: DNA
<213> ORGANISM: Artificial
<220> FEATURE:
<223> OTHER INFORMATION: Oligonucleotide

<400> SEQUENCE: 9
aggtagaaaa ttaagagaac aatttaataa tagaacaata gtctttaatc actc     54

<210> SEQ ID NO 10
<211> LENGTH: 54
<212> TYPE: DNA
<213> ORGANISM: Artificial
<220> FEATURE:
<223> OTHER INFORMATION: Oligonucleotide

<400> SEQUENCE: 10
aggtaaaaaa ttaagagaac aatttaataa tagaacaata gtctttaatc actc     54

<210> SEQ ID NO 11
<211> LENGTH: 54
<212> TYPE: DNA
<213> ORGANISM: Artificial
<220> FEATURE:
<223> OTHER INFORMATION: Oligonucleotide

<400> SEQUENCE: 11
aggtagaaaa ttaagagaac aatttaataa tagaacaata gtctttaacc actc     54

<210> SEQ ID NO 12
<211> LENGTH: 54
<212> TYPE: DNA
<213> ORGANISM: Artificial
<220> FEATURE:
<223> OTHER INFORMATION: Oligonucleotide
```

-continued

```
<400> SEQUENCE: 12
aggtagaaaa ttaagagaac aatttaataa tagaacaata gtctttaacc aatc        54

<210> SEQ ID NO 13
<211> LENGTH: 23
<212> TYPE: DNA
<213> ORGANISM: Artificial
<220> FEATURE:
<223> OTHER INFORMATION: Oligonucleotide

<400> SEQUENCE: 13
tgtacaagac ccaacaacaa tac                                         23

<210> SEQ ID NO 14
<211> LENGTH: 23
<212> TYPE: DNA
<213> ORGANISM: Artificial
<220> FEATURE:
<223> OTHER INFORMATION: Oligonucleotide

<400> SEQUENCE: 14
tgtacaagac ccagcaacaa tac                                         23

<210> SEQ ID NO 15
<211> LENGTH: 25
<212> TYPE: DNA
<213> ORGANISM: Artificial
<220> FEATURE:
<223> OTHER INFORMATION: Oligonucleotide

<400> SEQUENCE: 15
tgtacaagac ccaacaataa tacaa                                       25

<210> SEQ ID NO 16
<211> LENGTH: 25
<212> TYPE: DNA
<213> ORGANISM: Artificial
<220> FEATURE:
<223> OTHER INFORMATION: Oligonucleotide

<400> SEQUENCE: 16
tgtacaaggc ccaacaataa tacaa                                       25
```

SYSTEM AND METHOD FOR DETECTION OF HIV TROPISM VARIANTS

CROSS-REFERENCE TO RELATED APPLICATIONS

This application is a divisional of U.S. patent application Ser. No. 12/456,528, filed on Jun. 17, 2009 (now U.S. Pat. No. 7,888,034), which is related to and claims priority from U.S. Provisional Patent Application Ser. No. 61/077,356, titled "System and Method for Detection of HIV Tropism Variants", filed Jul. 1, 2008. The contents of each of these applications are incorporated herein by reference in their entireties.

FIELD OF THE INVENTION

The invention provides systems, methods, reagents, and kits for detecting and analyzing sequence variants associated with HIV-1 tropism in clades A, B, C, D, and G which account for the majority of infections encountered worldwide. In addition, the invention also provides utility for analysis of sequence variants in clades F, H, J and K which account for less than 1% of infections and for which the amount of sequence information available is limited. A powerful aspect of the invention is that the variants are detected in parallel from a population of target polynucleotides, such as for instance a population derived from a patient sample, and the allelic frequency of the variants in the population determined. The invention also includes analysis of the variant frequency for the determination of therapeutic regimen with the highest likelihood of desirable outcome.

BACKGROUND OF THE INVENTION

The Human Immunodeficiency Virus (generally referred to as HIV) continues to be a major problem worldwide, even though a plethora of compounds have been approved for treatment. Due to the error-prone nature of viral reverse transcriptase and the high viral turnover ($t_{1/2}$=1-3 days), the HIV genome mutates very rapidly. For example, reverse transcriptase is estimated to generate, on average, one mutation per replication of the 9.7 Kb genome that does not dramatically affect the ability of the virus to propagate. This leads to the formation of 'quasispecies', where many different mutants exist in a dynamic relationship.

HIV virus particles enter cells via the CD4 receptor and a co-receptor molecule. The co-receptor specificity of a given viral particle determines its tropism (The term "tropism" generally refers to the affinity of a viral particle for particular cell and receptor types). The majority of HIV-1 strains utilize the chemokine receptors CCR5 (R5 tropism), CXCR4 (X4 tropism) or both (R5X4 or dual tropism). Most newly infected individuals appear to have predominantly R5 tropic virus, and the SI phenotype has been associated with late-stage HIV infection and low CD4 cell counts as well as accelerated progression to AIDS. Additional examples of HIV tropism strains and their relationship to disease progression are described in Poveda et al., AIDS 2006, 20:1359-1367; Jensen et al., AIDS Rev 2003; 5:104-112; Jensen et al., Journal of Virology May 2006, p. 4698-4704; Jensen et al., Journal of Virology, December 2003, p. 13376-13388; and Nelson et al., Journal of Virology, November 1997, p. 8750-8758, each of which is hereby incorporated by reference herein in its entirety for all purposes.

There is currently only one FDA-approved drug that inhibits HIV entry by disrupting its interaction with a co-receptor, but more are in development. Maraviroc (also known as Selzentry, which is marketed by Pfizer Inc.) is a small molecule CCR5 inhibitor. Current recommendations published by the FDA state that each patient's HIV population be tested for tropism before Maraviroc is prescribed. This is due to the fact that clonal analysis of HIV quasispecies in patients that failed treatment during Maraviroc clinical trials revealed that small amounts of X4 tropic viruses were present before treatment initiation and it is thought that selection against CCR5 entry gave the X4 virus an advantage over the majority R5 strains. This mode of resistance development is analogous to the emergence of resistance to the 'classical' HIV drugs, i.e, protease and reverse transcriptase inhibitors, where a significant subset of HIV infected subjects carry pre-existing resistant strains prior to drug exposure—most likely due to primary infection by exposure to virus from treatment-experienced individuals. In addition to this pathway, resistant strains are continually generated de novo from wild type virus by replication under drug selective pressure due to the error-prone nature of the viral reverse transcriptase as described above. However, outgrowth of pre-existing resistant or, in the case of maraviroc treatment, X4 tropic virus, is more efficient under drug treatment and leads to accelerated treatment failure.

Viral tropism is determined by exposed amino acid sequences in the gp120 surface envelope protein. In particular, the V3 (third variable) region has been implicated in co-receptor usage selection. As the name implies, the approximately 35 amino acid long sequence is highly variable, but there are common features distinguishing R5 and X4 tropic viruses located within this sequence. A number of tropism prediction algorithms have been developed based directly on V3 sequences, and these are likely to be continually refined over the next few years. For example, several position specific scoring matrix (PSSM) algorithms that directly correlate amino acid residues in the V3 to tropism phenotypes (as well as these can be determined) have been published and some can even be accessed through the Internet.

Phenotypic tropism testing is now commercially available, but is expensive, labor intensive and time consuming. Additionally, phenotyping is heavily dependent on the efficient generation of a library of viral sequences, such that any cloning bias will generate a systematic testing error. Both phenotypic and sequence-based tropism determination is currently performed as population assays, which are, by their nature, less sensitive than assays based on clonal separation of each viral strain. However, clonal analysis is extremely labor intensive and requires testing of thousands of clones from each subject in order to achieve high sensitivity. Embodiments of the described invention include a sequence-based tropism determination assay wherein clonal sequences are obtained directly from viral RNA quasispecies without a labor intensive cloning step. Long read-length 454 sequencing available from 454 Life Science Corporation is ideally suited to generating thousands of clonal reads from multiple subjects in a single sequencing run. Further, embodiments of the described sequencing technologies enable what may be referred to as "Massively Parallel" capable of achieving a sensitivity of detection of low abundance variants that include a frequency of 1% or less of the allelic variants in a population. This, coupled with a tropism prediction algorithm provides a convenient method for quickly and efficiently obtaining tropism information at very high sensitivity.

SUMMARY OF THE INVENTION

Embodiments of the invention relate to the determination of the sequence of nucleic acids. More particularly, embodiments of the invention relate to methods and systems for correcting errors in data obtained during the sequencing of nucleic acids by SBS.

An embodiment of a method for detecting low frequency occurrence of one or more HIV sequence variants associated with drug resistance is described that comprises the steps of: generating cDNA species from each RNA molecule in an HIV sample population; amplifying at least one first amplicon from the cDNA species, wherein each first amplicon comprises a plurality of amplified copies and is amplified with a pair of nucleic acid primers that define a locus of the first amplicon; clonally amplifying the amplified copies of the first amplicons to produce a plurality of second amplicons wherein a plurality of the second amplicons comprise an immobilized population of substantially identical copies from one of the amplified copies of first amplicons; determining a nucleic acid sequence composition of the substantially identical copies from at least 100 of the immobilized populations in parallel on a single substrate; and detecting one or more sequence variants that occur at a frequency of 5% or less in the nucleic acid sequence composition of the at least 100 immobilized populations; and correlating the detected sequence variants with variation associated with HIV tropism.

In addition, a kit for performing the methods of the invention is described, wherein the kit comprises one or more pairs of primers selected from the group consisting of V3-1F and V3-1R; V3-2F and V3-2R; V3-1F and V3-2R; and V3-2F and V3-1R.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 160 appears first in FIG. 1). All of these conventions, however, are intended to be typical or illustrative, rather than limiting.

FIGS. 4A and 4B are simplified graphical examples of one embodiment of identified frequency of HIV tropism haplotypes associated with tropism types from an HIV sample. The sequences depicted in FIG. 4A correspond to the following sequences (from top to bottom): SEQ ID NO: 13, SEQ ID NO: 14, SEQ ID NO: 13, SEQ ID NO: 14, SEQ ID NO: 14, SEQ ID NO: 13, SEQ ID NO: 13, SEQ ID NO: 13, SEQ ID NO: 14, and SEQ ID NO: 14. In FIG. 4B, the sequences are as follows, from top to bottom: SEQ ID NO: 15, SEQ ID NO: 16, SEQ ID NO: 15, and SEQ ID NO: 15.

DETAILED DESCRIPTION OF THE INVENTION

Figure 1:
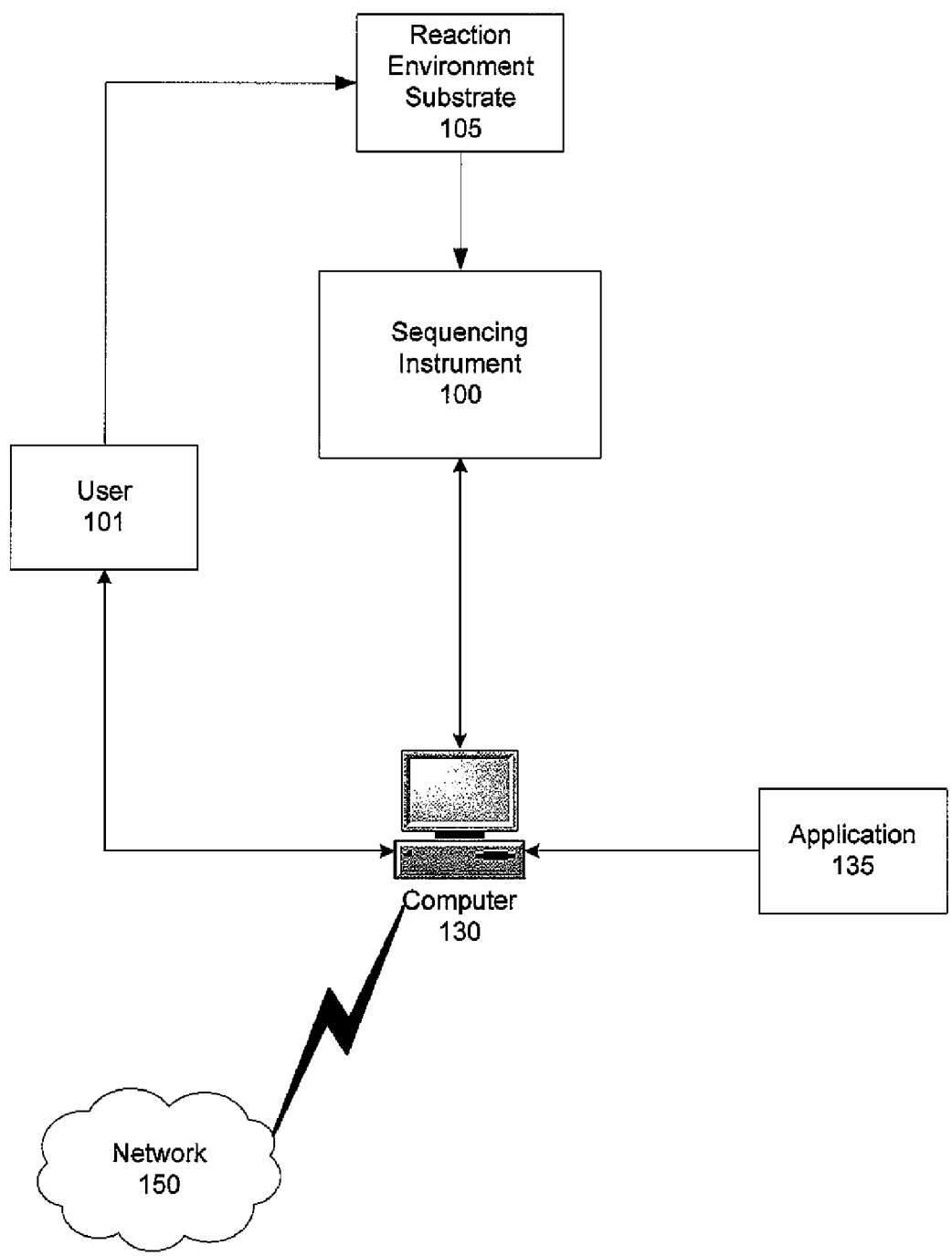
FIG. 1 is a functional block diagram of one embodiment of a sequencing instrument under computer control and a reaction substrate.

As will be described in greater detail below, embodiments of the presently described invention include systems, methods, and kits for targeted sequencing using primer species specific to amplify sequence regions comprising HIV variants, and using those amplified sequence regions for highly sensitive detection of the variants.

In particular, embodiments of the invention relate to investigating HIV tropism variation by sequencing in parallel a population of target nucleic acid sequences amplified from a sample, detecting each variant that is present in at least 1% of the population, and associating the detected variants with a therapeutic regimen. In one embodiment, one or more target regions from a representative proportion of the total population HIV virus in a sample are clonally replicated by polymerase chain reaction (PCR), where the clonal populations (also referred to as "amplicons") are each derived from a single viral particle. The clonal populations are sequenced in parallel to identify variants of previously known and unknown composition as well as the frequency of occurrence of each variant which is representative of the frequency of the variants in the original sample.

As described above, embodiments of the invention employ nucleic acid primers specifically designed to amplify the env region of HIV RNA or its complementary DNA, including what is referred to as the third variable region (hereafter referred to as the V3 region). Also, the target sequences for the primers have been specifically selected because of their proximity to the target region, and because they exhibit a low rate of mutation that predictably enable primer hybridization and amplification of the target nucleic regions in an HIV nucleic acid population. Thousands of individual HIV amplicons are sequenced in a massively parallel, efficient, and cost effective manner to generate a distribution of the sequence variants found in the population of HIV viral particles.

a. General

The term "flowgram" generally refers to a graphical representation of sequence data generated by SBS methods, particularly pyrophosphate based sequencing methods (also referred to as "pyrosequencing") and may be referred to more specifically as a "pyrogram".

The term "read" or "sequence read" as used herein generally refers to the entire sequence data obtained from a single nucleic acid template molecule or a population of a plurality of substantially identical copies of the template nucleic acid molecule.

The terms "run" or "sequencing run" as used herein generally refer to a series of sequencing reactions performed in a sequencing operation of one or more template nucleic acid molecules.

The term "flow" as used herein generally refers to a serial or iterative cycle of addition of solution to an environment comprising a template nucleic acid molecule, where the solution may include a nucleotide species for addition to a nascent molecule or other reagent such as buffers or enzymes that may be employed in a sequencing reaction or to reduce carryover or noise effects from previous flow cycles of nucleotide species.

The term "flow cycle" as used herein generally refers to a sequential series of flows where a nucleotide species is flowed once during the cycle (i.e. a flow cycle may include a sequential addition in the order of T, A, C, G nucleotide species, although other sequence combinations are also considered part of the definition). Typically the flow cycle is a repeating cycle having the same sequence of flows from cycle to cycle.

The term "read length" as used herein generally refers to an upper limit of the length of a template molecule that may be reliably sequenced. There are numerous factors that contribute to the read length of a system and/or process including, but not limited to the degree of GC content in a template nucleic acid molecule.

The term "test fragment", or "TF" as used herein generally refers to a nucleic acid element of known sequence composition that may be employed for quality control, calibration, or other related purposes.

A "nascent molecule" generally refers to a DNA strand which is being extended by the template-dependent DNA polymerase by incorporation of nucleotide species which are complementary to the corresponding nucleotide species in the template molecule.

The terms "template nucleic acid", "template molecule", "target nucleic acid", or "target molecule" generally refer to a nucleic acid molecule that is the subject of a sequencing reaction from which sequence data or information is generated.

The term "nucleotide species" as used herein generally refers to the identity of a nucleic acid monomer including purines (Adenine, Guanine) and pyrimidines (Cytosine, Uracil, Thymine) typically incorporated into a nascent nucleic acid molecule.

The term "monomer repeat" or "homopolymers" as used herein generally refers to two or more sequence positions comprising the same nucleotide species (i.e. a repeated nucleotide species).

The term "homogeneous extension", as used herein, generally refers to the relationship or phase of an extension reaction where each member of a population of substantially identical template molecules is homogenously performing the same extension step in the reaction.

The term "completion efficiency" as used herein generally refers to the percentage of nascent molecules that are properly extended during a given flow.

The term "incomplete extension rate" as used herein generally refers to the ratio of the number of nascent molecules that fail to be properly extended over the number of all nascent molecules.

The term "genomic library" or "shotgun library" as used herein generally refers to a collection of molecules derived from and/or representing an entire genome (i.e. all regions of a genome) of an organism or individual.

The term "amplicon" as used herein generally refers to selected amplification products such as those produced from Polymerase Chain Reaction or Ligase Chain Reaction techniques.

The term "variant", "quasispecies", or "allele" as used herein generally refer to one of a plurality of species each encoding a similar sequence composition but with a degree of distinction from each other. The distinction may include any type of genetic variation known to those of ordinary skill in the related art, that include but are not limited to single nucleotide polymorphisms (SNPs), insertions or deletions (the combination of insertion/deletion events are also referred to as "indels"), differences in the number of repeated sequences (also referred to as tandem repeats), and structural variation.

The term "allele frequency" or "allelic frequency" as used herein generally refers to the proportion of all variants in a population that is comprised of a particular variant.

The term "key sequence" or "key element" as used herein generally refers to a nucleic acid sequence element (typically of about 4 sequence positions, i.e. TGAC or other combination of nucleotide species) associated with a template nucleic acid molecule in a known location (i.e. typically included in a ligated adaptor element) comprising known sequence composition that is employed as a quality control reference for sequence data generated from template molecules. The sequence data passes the quality control if it includes the known sequence composition associated with a Key element in the correct location.

The term "keypass" or "keypass well" as used herein generally refers to the sequencing of a full length nucleic acid test sequence of known sequence composition (i.e., a "test fragment" or "TF" as referred to above) in a reaction well, where the accuracy of the sequence derived from keypass test sequence is compared to the known sequence composition and used to measure of the accuracy of the sequencing and for quality control. In typical embodiments a proportion of the total number of wells in a sequencing run will be keypass wells which may in some embodiments be regionally distributed.

The term "blunt end" as used herein is interpreted consistently with the understanding of one of ordinary skill in the related art and generally refers to a linear double stranded nucleic acid molecule having an end that terminates with a pair of complementary nucleotide base species, where a pair of blunt ends are always compatible for ligation to each other.

The term "sticky end" or "overhang" as used herein is interpreted consistently with the understanding of one of ordinary skill in the related art and generally refers to a linear double stranded nucleic acid molecule having one or more unpaired nucleotide species at the end of one strand of the molecule, where the unpaired nucleotide species may exist on either strand and include a single base position or a plurality of base positions (also sometimes referred to as "cohesive end").

The term "bead" or "bead substrate" as used herein generally refers to any type of bead of any convenient size and fabricated from any number of known materials such as cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase bead supports known to those of skill in the art.

Some exemplary embodiments of systems and methods associated with sample preparation and processing, generation of sequence data, and analysis of sequence data are generally described below, some or all of which are amenable for use with embodiments of the presently described invention. In particular the exemplary embodiments of systems and methods for preparation of template nucleic acid molecules, amplification of template molecules, generating target specific amplicons and/or genomic libraries, sequencing methods and instrumentation, and computer systems are described.

In typical embodiments, the nucleic acid molecules derived from an experimental or diagnostic sample must be prepared and processed from its raw form into template molecules amenable for high throughput sequencing. The processing methods may vary from application to application resulting in template molecules comprising various characteristics. For example, in some embodiments of high throughput sequencing it is preferable to generate template molecules with a sequence or read length that is at least the length a particular sequencing method can accurately produce sequence data for. In the present example, the length may include a range of about 25-30 base pairs, about 50-100 base pairs, about 200-300 base pairs, about 350-500 base pairs, greater than 500 base pairs, or other length amenable for a particular sequencing application. In some embodiments, nucleic acids from a sample, such as a genomic sample, are fragmented using a number of methods known to those of ordinary skill in the art. In preferred embodiments, methods that randomly fragment (i.e. do not select for specific sequences or regions) nucleic acids and may include what is referred to as nebulization or sonication methods. It will however, be appreciated that other methods of fragmentation such as digestion using restriction endonucleases may be employed for fragmentation purposes. Also in the present example, some processing methods may employ size selection methods known in the art to selectively isolate nucleic acid fragments of the desired length.

Also, it is preferable in some embodiments to associate additional functional elements with each template nucleic acid molecule. The elements may be employed for a variety of functions including, but not limited to, primer sequences for amplification and/or sequencing methods, quality control elements, unique identifiers (also referred to as a multiplex identifier or "MID") that encode various associations such as with a sample of origin or patient, or other functional element. Some or all of the described functional elements may be combined into adaptor elements that are coupled to nucleotide sequences in certain processing steps. For example, some embodiments may associate priming sequence elements or regions comprising complementary sequence composition to primer sequences employed for amplification and/or sequencing. Further, the same elements may be employed for what may be referred to as "strand selection" and immobilization of nucleic acid molecules to a solid phase substrate. In some embodiments two sets of priming sequence regions (hereafter referred to as priming sequence A, and priming sequence B) may be employed for strand selection where only single strands having one copy of priming sequence A and one copy of priming sequence B is selected and included as the prepared sample. In alternative embodiments, design characteristics of the adaptor elements eliminate the need for strand selection. The same priming sequence regions may be employed in methods for amplification and immobilization where, for instance priming sequence B may be immobilized upon a solid substrate and amplified products are extended therefrom.

Additional examples of sample processing for fragmentation, strand selection, and addition of functional elements and adaptors are described in U.S. patent application Ser. No. 10/767,894, titled "Method for Preparing Single-Stranded DNA Libraries", filed Jan. 28, 2004; U.S. patent application Ser. No. 12/156,242, titled "System and Method for Identification of Individual Samples from a Multiplex Mixture", filed May 29, 2008; and U.S. patent application Ser. No. 12/380,139, titled "System and Method for Improved Processing of Nucleic Acids for Production of Sequencable Libraries", filed Feb. 23, 2009, each of which is hereby incorporated by reference herein in its entirety for all purposes.

Various examples of systems and methods for performing amplification of template nucleic acid molecules to generate populations of substantially identical copies are described. It will be apparent to those of ordinary skill that it is desirable in some embodiments of SBS to generate many copies of each nucleic acid element to generate a stronger signal when one or more nucleotide species is incorporated into each nascent molecule associated with a copy of the template molecule. There are many techniques known in the art for generating copies of nucleic acid molecules such as, for instance, amplification using what are referred to as bacterial vectors, "Rolling Circle" amplification (described in U.S. Pat. Nos. 6,274,320 and 7,211,390, incorporated by reference above) and Polymerase Chain Reaction (PCR) methods, each of the techniques are applicable for use with the presently described invention. One PCR technique that is particularly amenable to high throughput applications include what are referred to as emulsion PCR methods (also referred to as emPCR™ methods).

Typical embodiments of emulsion PCR methods include creating a stable emulsion of two immiscible substances creating aqueous droplets within which reactions may occur. In particular, the aqueous droplets of an emulsion amenable for use in PCR methods may include a first fluid such as a water based fluid suspended or dispersed as droplets (also referred to as a discontinuous phase) within another fluid such as a hydrophobic fluid (also referred to as a continuous phase) that typically includes some type of oil. Examples of oil that may be employed include, but are not limited to, mineral oils, silicone based oils, or fluorinated oils.

Further, some emulsion embodiments may employ surfactants that act to stabilize the emulsion that may be particularly useful for specific processing methods such as PCR. Some embodiments of surfactant may include one or more of a silicone or fluorinated surfactant. For example, one or more non-ionic surfactants may be employed that include but are not limited to sorbitan monooleate (also referred to as Span™ 80), polyoxyethylenesorbitsan monooleate (also referred to as Tween™ 80), or in some preferred embodiments dimethicone copolyol (also referred to as Abil® EM90), polysiloxane, polyalkyl polyether copolymer, polyglycerol esters, poloxamers, and PVP/hexadecane copolymers (also referred to as Unimer U-151), or in more preferred embodiments a high molecular weight silicone polyether in cyclopentasiloxane (also referred to as DC 5225C available from Dow Corning).

The droplets of an emulsion may also be referred to as compartments, microcapsules, microreactors, microenvironments, or other name commonly used in the related art. The aqueous droplets may range in size depending on the composition of the emulsion components or composition, contents contained therein, and formation technique employed. The described emulsions create the microenvironments within which chemical reactions, such as PCR, may be performed. For example, template nucleic acids and all reagents necessary to perform a desired PCR reaction may be encapsulated and chemically isolated in the droplets of an emulsion. Additional surfactants or other stabilizing agent may be employed in some embodiments to promote additional stability of the droplets as described above. Thermocycling operations typical of PCR methods may be executed using the droplets to amplify an encapsulated nucleic acid template resulting in the generation of a population comprising many substantially identical copies of the template nucleic acid. In some embodiments, the population within the droplet may be referred to as a "clonally isolated", "compartmentalized", "sequestered", "encapsulated", or "localized" population. Also in the present example, some or all of the described droplets may further encapsulate a solid substrate such as a bead for attachment of template and amplified copies of the template, amplified copies complementary to the template, or combination thereof. Further, the solid substrate may be enabled for attachment of other type of nucleic acids, reagents, labels, or other molecules of interest.

Embodiments of an emulsion useful with the presently described invention may include a very high density of droplets or microcapsules enabling the described chemical reactions to be performed in a massively parallel way. Additional examples of emulsions employed for amplification and their uses for sequencing applications are described in U.S. patent application Ser. Nos. 10/861,930; 10/866,392; 10/767,899; 11/045,678 each of which are hereby incorporated by reference herein in its entirety for all purposes.

Also, embodiments that generate target specific amplicons for sequencing may be employed with the presently described invention that include using sets of specific nucleic acid primers to amplify a selected target region or regions from a sample comprising the target nucleic acid. Further, the sample may include a population of nucleic acid molecules that are known or suspected to contain sequence variants and the primers may be employed to amplify and provide insight into the distribution of sequence variants in the sample. For example a method for identifying a sequence variant by specific amplification and sequencing of multiple alleles in a nucleic acid sample may be performed. The nucleic acid is first subjected to amplification by a pair of PCR primers designed to amplify a region surrounding the region of interest or segment common to the nucleic acid population. Each of the products of the PCR reaction (first amplicons) is subsequently further amplified individually in separate reaction vessels such as an emulsion based vessel described above. The resulting amplicons (referred to herein as second amplicons), each derived from one member of the first population of amplicons, are sequenced and the collection of sequences, from different emulsion PCR amplicons (i.e. second amplicons), are used to determine an allelic frequency.

Some advantages of the described target specific amplification and sequencing methods include a higher level of sensitivity than previously achieved. Further, embodiments that employ high throughput sequencing instrumentation such as for instance embodiments that employ what is referred to as a PicoTiterPlate® array (also sometimes referred to as a PTP™ plate or array) of wells provided by 454 Life Sciences Corporation, the described methods can be employed to generate sequence composition for over 100,000, over 300,000, over 500,000, or over 1,000,000 nucleic acid regions per run or experiment and may depend, at least in part, on user preferences such as lane configurations enabled by the use of gaskets etc. Also, the described methods provide a sensitivity of detection of low abundance alleles which may represent 1% or less of the allelic variants. Another advantage of the methods includes generating data comprising the sequence of the analyzed region. Importantly, it is not necessary to have prior knowledge of the sequence of the locus being analyzed.

Additional examples of target specific amplicons for sequencing are described in U.S. patent application Ser. No. 11/104,781, titled "Methods for Determining Sequence Variants Using Ultra-Deep Sequencing", filed Apr. 12, 2005; and PCT Patent Application Serial No. US 2008/003424, titled "System and Method for Detection of HIV Drug Resistant Variants", filed Mar. 14, 2008, each of which is hereby incorporated by reference herein in its entirety for all purposes.

Further, embodiments of sequencing may include Sanger type techniques, techniques generally referred to as Sequencing by Hybridization (SBH), Sequencing by Ligation (SBL), or Sequencing by Incorporation (SBI) techniques. Further, the sequencing techniques may include what is referred to as polony sequencing techniques; nanopore, waveguide and other single molecule detection techniques; or reversible terminator techniques. As described above a preferred technique may include Sequencing by Synthesis methods. For example, some SBS embodiments sequence populations of substantially identical copies of a nucleic acid template and typically employ one or more oligonucleotide primers designed to anneal to a predetermined, complementary position of the sample template molecule or one or more adaptors attached to the template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide species that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. It will also be appreciated that the process of adding a nucleotide species to the end of a nascent molecule is substantially the same as that described above for addition to the end of a primer.

As described above, incorporation of the nucleotide species can be detected by a variety of methods known in the art, e.g. by detecting the release of pyrophosphate (PPi) (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include but are not limited to mass tags and fluorescent or chemiluminescent labels. In typical embodiments, unincorporated nucleotides are removed, for example by washing. Further, in some embodiments the unincorporated nucleotides may be subjected to enzymatic degradation such as, for instance, degradation using the apyrase or pyrophosphatase enzymes as described in U.S. patent application Ser. No. 12/215,455, titled "System and Method for Adaptive Reagent Control in Nucleic Acid Sequencing", filed Jun. 27, 2008; and titled "System and Method for Improved Signal Detection in Nucleic Acid Sequencing", filed Jan. 29, 2009; each of which is hereby incorporated by reference herein in its entirety for all purposes.

In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, extension, signal acquisition, and washing result in a determination of the nucleotide sequence of the template strand. Continuing with the present example, a large number or population of substantially identical template molecules (e.g. $10^3$, $10^4$, $10^5$, $10^6$ or $10^7$ molecules) are typically analyzed simultaneously in any one sequencing reaction, in order to achieve a signal which is strong enough for reliable detection.

In addition, it may be advantageous in some embodiments to improve the read length capabilities and qualities of a sequencing process by employing what may be referred to as a "paired-end" sequencing strategy. For example, some embodiments of sequencing method have limitations on the total length of molecule from which a high quality and reliable read may be generated. In other words, the total number of sequence positions for a reliable read length may not exceed 25, 50, 100, or 500 bases depending on the sequencing embodiment employed. A paired-end sequencing strategy extends reliable read length by separately sequencing each end of a molecule (sometimes referred to as a "tag" end) that comprise a fragment of an original template nucleic acid molecule at each end joined in the center by a linker sequence. The original positional relationship of the template fragments is known and thus the data from the sequence reads may be re-combined into a single read having a longer high quality read length. Further examples of paired-end sequencing embodiments are described in U.S. patent application Ser. No. 11/448,462, titled "Paired End Sequencing", filed Jun. 6, 2006, and in U.S. patent application Ser. No. 12/322,119, titled "Paired End Sequencing", filed Jan. 28, 2009, each of which is hereby incorporated by reference herein in its entirety for all purposes.

Some examples of SBS apparatus may implement some or all of the methods described above and may include one or more of a detection device such as a charge coupled device (i.e. CCD camera) or a confocal type architecture, a microfluidics chamber or flow cell, a reaction substrate, and/or a pump and flow valves. Taking the example of pyrophosphate based sequencing, embodiments of an apparatus may employ a chemiluminescent detection strategy that produces an inherently low level of background noise.

In some embodiments, the reaction substrate for sequencing may include what is referred to as a PTP™ array, as described above, formed from a fiber optics faceplate that is acid-etched to yield hundreds of thousands or more of very small wells each enabled to hold a population of substantially identical template molecules (i.e. some preferred embodiments comprise about 3.3 million wells on a 70×75 mm PTP™ array at a 35 μm well to well pitch). In some embodiments, each population of substantially identical template molecule may be disposed upon a solid substrate such as a bead, each of which may be disposed in one of said wells. For example, an apparatus may include a reagent delivery element for providing fluid reagents to the PTP plate holders, as well as a CCD type detection device enabled to collect photons of light emitted from each well on the PTP plate. An example of reaction substrates comprising characteristics for improved signal recognition is described in U.S. patent application Ser. No. 11/215,458, titled "THIN-FILM COATED MICROWELL ARRAYS AND METHODS OF MAKING SAME", filed Aug. 30, 2005, which is hereby incorporated by reference herein in its entirety for all purposes. Further examples of apparatus and methods for performing SBS type sequencing and pyrophosphate sequencing are described in U.S. Pat. No. 7,323,305 and U.S. patent application Ser. No. 11/195,254 both of which are incorporated by reference above.

In addition, systems and methods may be employed that automate one or more sample preparation processes, such as the emPCR™ process described above. For example, automated systems may be employed to provide an efficient solution for generating an emulsion for emPCR processing, performing PCR Thermocycling operations, and enriching for successfully prepared populations of nucleic acid molecules for sequencing. Examples of automated sample preparation systems are described in U.S. patent application Ser. No. 11/045,678, titled "Nucleic acid amplification with continuous flow emulsion", filed Jan. 28, 2005, which is hereby incorporated by reference herein in its entirety for all purposes.

Also, the systems and methods of the presently described embodiments of the invention may include implementation of some design, analysis, or other operation using a computer readable medium stored for execution on a computer system. For example, several embodiments are described in detail below to process detected signals and/or analyze data generated using SBS systems and methods where the processing and analysis embodiments are implementable on computer systems.

An exemplary embodiment of a computer system for use with the presently described invention may include any type of computer platform such as a workstation, a personal computer, a server, or any other present or future computer. It will, however, be appreciated by one of ordinary skill in the art that the aforementioned computer platforms as described herein are specifically configured to perform the specialized operations of the described invention and are not considered general purpose computers. Computers typically include known components such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Centrino®, Core™ 2, Itanium® or Pentium® processor made by Intel Corporation, a SPARC® processor made by Sun Microsystems, an Athalon™ or Opteron™ processor made by AMD corporation, or it may be one of other processors that are or will become available. Some embodiments of a processor may include what is referred to as Multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows®-type operating system (such as Windows® XP or Windows Vista®) from the Microsoft Corporation; the Mac OS X operating system from Apple Computer Corp. (such as Mac OS X v10.5 "Leopard" or "Snow Leopard" operating systems); a Unix® or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example some commonly employed web browsers include Microsoft® Internet Explorer 7 available from Microsoft Corporation, Mozilla Firefox® 2 from the Mozilla Corporation, Safari 1.2 from Apple Computer Corp., or other type of web browser currently known in the art or to be developed in the future. Also, in the same or other embodiments an internet client may include, or could be an element of, specialized software applications enabled to access remote information via a network such as a data processing application for SBS applications. A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the interne, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some com- b. Embodiments of the Presently Described Invention

As described above, the invention relates to methods of detecting HIV tropism sequence variants from a sample and the identification of the tropism types present in said sample by associating the variant sequence composition with R5 or X4 tropism types. In particular embodiments of the invention include a two stage PCR technique (i.e. producing first and second amplicons as described above) targeted to regions of HIV known to be associated with tropism variants, coupled with a sequencing technique that produces sequence information from thousands of viral particles in parallel which enables identification of the occurrence of HIV tropism types (based upon an association of the tropism types with the detected sequence composition of variants in the sample), even those types occurring at a low frequency in a sample. In fact, embodiments of the invention can detect tropism sequence variants which are present in a sample containing HIV viral particles in non-stoichiometric allele amounts, such as, for example, HIV tropism variants present in less than 50%, less than 25%, less than 10%, less than 5% or less than 1%. The described embodiments enable such identification in a rapid, reliable, and cost effective manner.

Typically, one or more instrument elements may be employed that automate one or more process steps. For example, embodiments of a sequencing method may be executed using instrumentation to automate and carry out some or all process steps. FIG. 1 provides an illustrative example of sequencing instrument 100 that comprises an optic subsystem and a fluidic subsystem. Embodiments of sequencing instrument 100 employed to execute sequencing processes may include various fluidic components in the fluidic subsystem, various optical components in the optic subsystem, as well as additional components not illustrated in FIG. 1 that may include microprocessor and/or microcontroller components for local control of some functions. Further, as illustrated in FIG. 1 sequencing instrument 100 may be operatively linked to one or more external computer components such as computer 130 that may for instance execute system software or firmware such as application 135 that may provide instructional control of one or more of the components and/or some data analysis functions. In the same or alternative embodiments computer 130 may be linked to another computer, intranet, or internet via network 150. In the present example, sequencing instrument 100 and/or computer 130 or network 150 may include some or all of the components and characteristics of the embodiments generally described above.

Figure 2A:
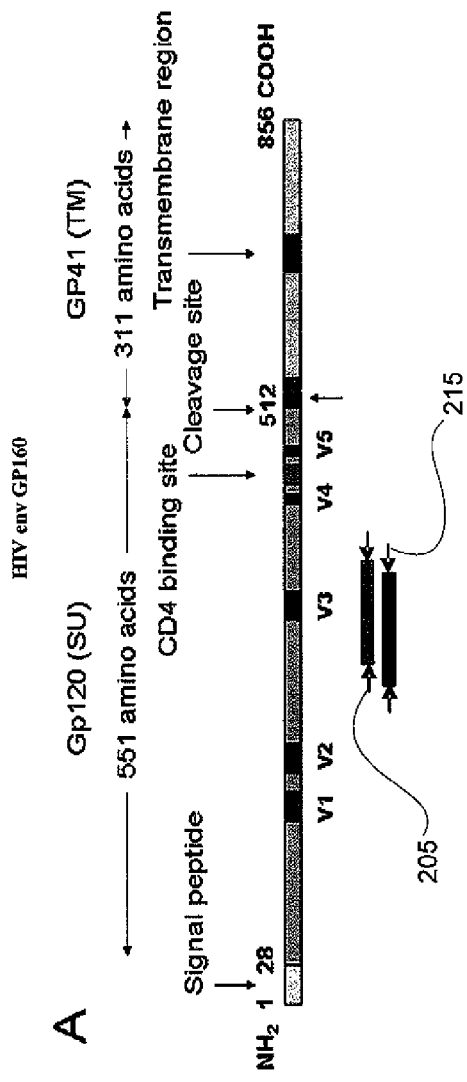
FIGS. 2A and 2B are simplified graphical examples of an embodiment of the positional relationship of amplicons and primer species relative to the HIV V3 env region.
Figure 2B:
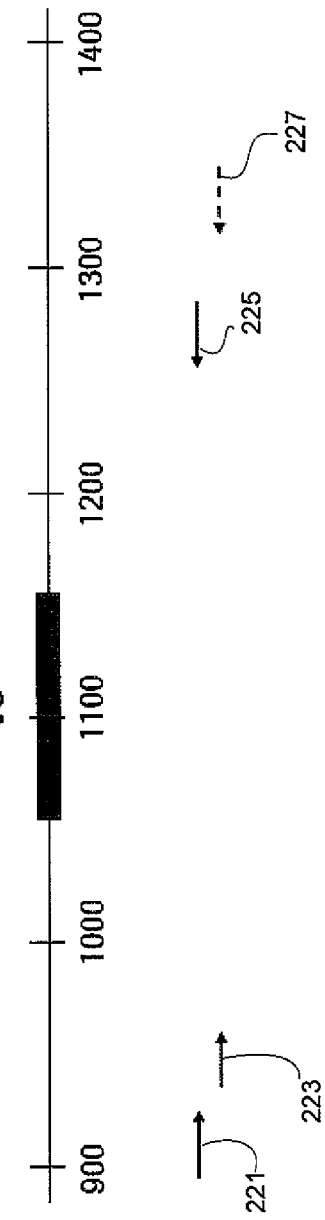

In one aspect of the invention, target specific primers were designed from an alignment of over 10,000 known HIV env sequences designed to generate, in an extremely low-bias manner, at least two amplicons for direct use in the described sequencing application. FIG. 2A provides an illustrative example of amplicon 205 and amplicon 215 generated from the primers. In FIG. 2A amplicons 205 and 215 are arranged in a staggered relationship spanning the V3 region, however it will be appreciated that amplicons 205 and 215 are exemplary and should not be considered as limiting. For instance, amplicons 205 and 215 can be produced from different primer combinations and have different lengths and coverage. FIG. 2B illustrates primers 221, 223, 225, and 227 where amplicon 205 as illustrated in FIG. 2A may be produced using the combination of primers 223 and 227 and amplicon 215 produced using primers 221 and 225. Alternatively, it may be advantageous to produce different amplicon products using different primer combinations such as amplicon products having a short amplicon product within the region covered by a long amplicon product where the region covered by the short product is represented in both amplicons. Both strategies provide regions with "double coverage" by the amplicons which is beneficial in the event that one of the amplicon products fails to amplify properly. In the present example, the long amplicon product could be generated using primers 221 and 227 and the short amplicon product generated using primers 223 and 225. It will also be appreciated that up to 4 amplicons can be generated using the primer combinations which include both the "staggered" and "short/long" amplicon strategies. In some embodiments, each amplicon is generated in a separate reaction using the associated primer combination. Alternatively, the primers may be pooled and amplified in a single reaction chamber where there are representative products from the different combinations. For example, primers 221, 223, and 225 may be combined into a single reaction vessel (i.e. excluding primer 227) resulting in two amplicon products of different lengths. Although, this approach may have a limitation in some conditions where one amplicon may be preferentially generated over another.

Those of ordinary skill in the related art will also appreciate that a "nested" type amplification strategy may be employed using primer 221, 223, 225, and 227. For example, nested PCR strategies are generally employed to reduce the effects of contamination typically caused by multiple primer binding sites and the generation of undesirable amplification products. In the present example, a first set of amplification products may be produced using forward primer 221 and reverse primer 227 which may contain some of the undesirable product. A second round of amplification using forward primer 223 and reverse primer 225 and the first set of amplification products may then be executed where it is unlikely that the undesirable products of the first set would have binding sites for primers 223 and 225 resulting in a set of amplification products with much higher specificity to the desired target region.

In some embodiments the combination of primers 221/223 and 225/227 respectively target highly conserved regions of sufficient length to accommodate both primers in the combination (i.e. both forward primer species or reverse primer species). In fact, there may be conserved regions closer to the V3 region that lack the sufficient length to design both primer species to the target which may be less desirable due to the restricted length. However, the sequencing technology described herein provides a sufficient read length that allows the primers to target regions farther away while providing full coverage of the V3 region. In fact, sequencing technologies with read lengths below 300 bp are not able to sequence through the entire V3 region using the described primer species due to their limited read lengths. In fact, complete sequences from each virus at the clonal level are required for the predictive algorithms, since sequence composition at each end of the V3 region are important for accurate prediction of tropism type. In the same or alternative embodiments, using the two amplicon approach (i.e. of first amplicons) with the described primer combinations improves the coverage and clade compatibility that is desirable, particularly for diagnostic type applications. For example, using a two first amplicon approach results in a more robust assay that a single first amplicon approach does not provide. Firstly, targeting generation of two amplicons provides redundancy so that should one amplicon fail to be generated, such as for instance due to the occurrence of an unpredicted SNP or other unknown sequence composition in the target region, there is a substantial likelihood that the other amplicon is successfully generated which allows the process to proceed. In addition, in some embodiments, such as the described staggered first amplicon approach, there is a greater likelihood that both amplicons would be successfully generated and sequenced with greater coverage of the V3 region because of the efficiency of sequencing the entire amplicon from beginning to end.

Importantly, the primer sets were specifically designed for the purpose of amplifying the vast majority of sequences in a mix, since clinical samples contain multiple viruses. For example, at least one of the amplicons generates from >99.4% of all (>10,000) clade B and C quasispecies listed in the Los Alamos public sequence database. This enables very low bias amplification and fast clonal sequencing of all sequences present in clinical plasma samples, whereby all variation (at both high and low frequencies) can be detected across the entire V3 region. In fact, the primers of the invention are compatible with clades A, B, C, D, and G which account for the majority of HIV infections worldwide. As those of ordinary skill appreciate, clade (also referred to as subtype) C accounted for 50% of infections worldwide in 2004, A-12%, B-10%, G-6%, and D-3%. As described above, it is believed that the primers of the invention are also compatible with clades F, H, J, and K which combined accounted for 0.94% of HIV infections worldwide in 2004, but the specificity of the primer sequences cannot be confirmed due to the disparity of adequate sequence information. Those of ordinary skill will also appreciate that currently there are 9 identified clades designated by letters A-K, where certain clade types are associated with specific geographical areas. For instance, HIV clade B is generally found in North America and Europe while clade C is generally found in South Africa and India.

Alignments of known HIV sequences may be performed using methods known to those of ordinary skill in the related art. For example, numerous sequence alignment methods, algorithms, and applications are available in the art including but not limited to the Smith-Waterman algorithm (Smith T F, Waterman M S (1981). "Identification of Common Molecular Subsequences". *Journal of Molecular Biology* 147: 195-197, which is hereby incorporated by reference herein in its entirety for all purposes), BLAST algorithm (Altschul, S. F., Gish, W., Miller, W., Myers, E. W. & Lipman, D. J. (1990) "Basic local alignment search tool." J. Mol. Biol. 215:403-410, which is hereby incorporated by reference herein in its entirety for all purposes), and Clustal (Thompson J D, Gibson T J, Plewniak F, Jeanmougin F, Higgins D G (1997). The ClustalX windows interface: flexible strategies for multiple sequence alignment aided by quality analysis tools. *Nucleic Acids Research,* 25:4876-4882, which is hereby incorporated by reference herein in its entirety for all purposes). The alignment of sequences into a single sequence provides a consensus of the most frequent sequence composition of the population of HIV sequences. Also in the present example, a software application may plot regions of interest for tropism typing as well as target regions for primer sequences against the aligned consensus sequence. Regions of interest include regions that are known to be susceptible to mutation and may contribute to the viral tropism type. Primer sets may then be designed to regions of the consensus sequence that are more conserved (i.e. less likely to mutate) than the regions of known mutation susceptibility. The primer sets disclosed herein were designed to regions of the consensus sequence that are more conserved (i.e. less likely to mutate) than the regions of known mutation susceptibility. The advantage of targeting sequence regions with a low mutation rate for primer design includes the ability to reliably use the designed primers without substantial risk of failure due to variation at the target region that would render the primer unable to bind, as well as the possibility of using the same primer sets for multiple clades. In addition, those of ordinary skill in the art appreciate that certain positions within what may be considered "conserved" regions of the consensus sequence may still be variable in their composition and are considered "degenerate" positions. In some preferred embodiments, parameters used for primer design include inserting a degenerate base at a position in the primer composition in cases where there is less than 98% frequency of a nucleotide species at that position in a multiple sequence alignment used to determine the consensus sequence. In addition, other parameters that affect the selection of the binding target region and primer composition include restricting degenerate positions to those that have only two alternative nucleotide species, as well as restricting the primer composition to no more than two degenerate positions to reduce the risk of forming primer dimers in the amplification reaction. It is also desirable in some embodiments to restrict the degenerate positions to the last 5 sequence positions of the primer composition (i.e. at the 3' end of the forward primer and the 5' end of the reverse primer) because it is advantageous to have the last 5 positions are highly conserved for binding efficiency. For example, a degenerate sequence position typically has multiple possible different nucleotide species that occur as alternative sequence composition at that position. Degenerate bases are well known in the art and various types of degeneracy are represented by IUPAC symbols that signify the alternative nucleotide compositions associated with the type. For example, the IUPAC symbol R represents that the purine bases (i.e. A and G) are alternative possibilities.

Embodiments of the described invention include the following primer species designed to produce at least two amplicons amenable for high throughput sequencing:

```
V3-1F Primer
5' TCAGCACAGTACARTGYACACATGG 3'    (SEQ ID NO: 1)

V3-1R Primer
5' CATTACAATTTCTRGGTCYCCTCC 3'     (SEQ ID NO: 2)

V3-2F Primer
5' CAACTCAACTRCTGTTAAATGGYAG 3'    (SEQ ID NO: 3)

V3-2R Primer
5' TGTTGTATTACAGTAGAARAAYTC 3'     (SEQ ID NO: 4)
```

Those of ordinary skill in the art will appreciate that some variability of sequence composition for primer sets exist and that 90% or greater homology to the disclosed primer sequences are considered within the scope of the presently described invention. For example, the target regions for the sets of primers may be slightly shifted and thus some difference in primer sequence composition is expected. Also, refinements to the consensus sequence may be made indicating a slight difference of sequence composition in the target region, and similarly some variation in primer sequence composition is expected.

As described above, at least two amplicons are produced using the primer embodiments described of the invention. For instance, those of ordinary skill will appreciate that both the short/long and staggered amplicon approaches may be employed simultaneously which provides essentially 4× coverage of the V3 region. If the staggered amplicon strategy is employed the V3-1 amplicon comprises an average length of 389 bp, and the V3-2 amplicon comprises an average length of 393 bp. Alternatively, if the staggered short/long strategy is employed the V3-short amplicon comprises an average length of 348 bp, and the V3-long amplicon comprises an average length of 434 bp. In addition, the primer embodiments of the described invention reliably and robustly produce the desired amplicons. For example, using the short/long amplicon strategy (i.e. short amplicon produced from V3-2F-V3-1R; and long amplicon produced from V3-1F-V3-2R) amplicons were generated at a concentration of between 113 and 242 ng/µl. Also using the staggered amplicon strategy (i.e. one amplicon produced from V3-1F-V3-1R; and a second amplicon produced from V3-2 F-V3-2R) amplicons were generated at a concentration of between 113 and 251 ng/µl.

In some embodiments, adaptor elements are ligated to the ends of the amplicons that comprise another general primer used for a second round of amplification from the individual amplicons producing a population of clonal copies (i.e. to generate second amplicons). It will be appreciated that the adaptors may also include other elements as described elsewhere in this specification such as quality control elements, other primers such as a sequencing primer and/or amplification primer (or single primer enabled to function as both an amplification and sequencing primer), unique identifier elements (i.e. MID elements as described above), and so on. Also, in some embodiments the target specific primers described above may be combined with one or more of the other elements useable in subsequent process steps. For example, a single stranded nucleic acid molecule may comprise the target specific primer sequence at one end with additional sequence elements adjacent. The target specific primer hybridizes to the target region may with the other elements hanging off due to the non-complementary nature of their sequence composition to the flanking sequence next to the target region, where the amplification product includes a copy of the region of interest as well as the additional sequence elements.

In some embodiments of the invention, a first strand cDNA is generated from HIV RNA using the target specific primers. In one embodiment, a first strand cDNA may be generated using a single primer such as the V3-1R primer that lacks a sequencing adaptor (also referred to as a SAD) as described below with respect to the method described in FIG. 5. Subsequently, at least two amplicons are produced (i.e. amplicons the short/long or staggered strategies, or a combination of one or more amplicon members from both strategies) using the target specific primer/processing elements strategy. The resulting amplicons thus comprise the necessary processing elements due to their association with the primer.

Also in preferred embodiments the second round of amplification occurs using the emulsion based PCR amplification strategy described above that typically results in an immobilized clonal population of second amplicons on a bead substrate that effectively sequesters the second amplicons preventing diffusion when the emulsion is broken. Typically, thousands of the second amplicons are then sequenced in parallel as described elsewhere in this specification. For example, beads with immobilized populations of second amplicons may be loaded onto reaction environment substrate 105 and processed using sequencing instrument 100 which generates >1000 clonal reads from each sample and outputs the sequence data to computer 130 for processing. Computer 130 executes specialized software to identify variants at 1% abundance or below from the sample.

Figure 3:
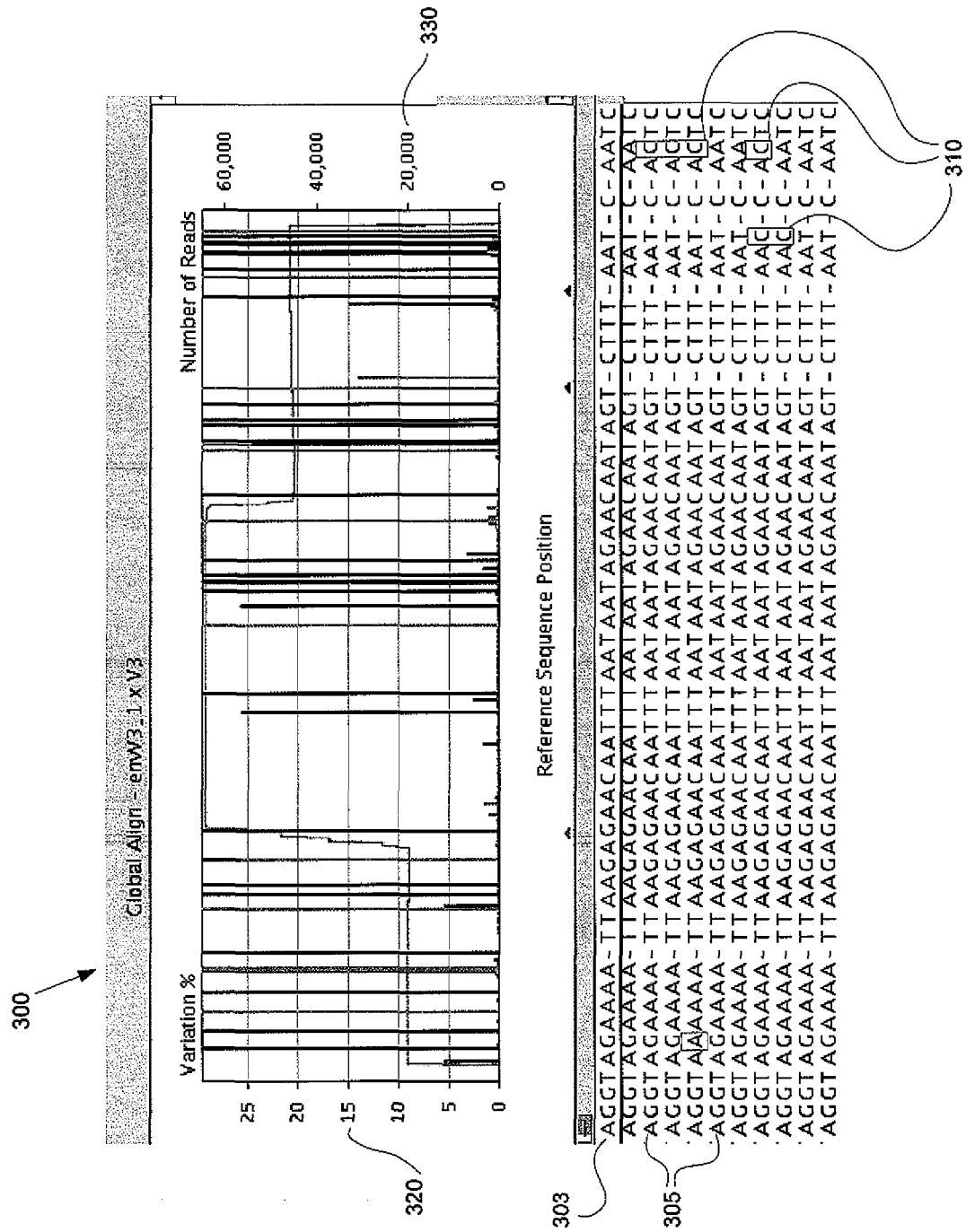
FIG. 3 is a simplified graphical example of one embodiment of a comparison of sequence data obtained from multiple HIV RNA against a consensus sequence for a section of the HIV V3 region. The sequences provided in FIG. 3, from top to bottom, are as follows: SEQ ID NO: 8, SEQ ID NO: 8, SEQ ID NO: 9, SEQ ID NO: 9, SEQ ID NO: 10, SEQ ID NO: 8, SEQ ID NO: 8, SEQ ID NO: 11, SEQ ID NO: 12, SEQ ID NO: 8, and SEQ ID NO: 8.

FIG. 3 provides an illustrative example of the output of sequence analysis software and includes interface 300 that includes multiple panes and provides user 101 with a visual representation of consensus sequence 303 aligned with a plurality of sequences 305 each from a single read from an individual HIV RNA molecule. Interface 300 also identifies base calls 310 that differ in sequence composition from consensus sequence 303, where such identification may include highlighting base call 310 in a different color, bold, italic, or other visual means of representation known in the related art. Interface 300 also provides user 101 with a visual representation of the level of detected variation 320 in the sample by base position in reference sequence 303 as well as a representation of the number of sequence reads 330 at those base positions. In the example of FIG. 3, variants that occur at a frequency of 1% or less in the sample are easily determined by examination of the clonal reads. In the example shown, >60,000 reads (either forward or reverse sequencing direction) with full or partial V3 coverage were generated from a clinical sample.

The sequence data may also be further analyzed by the same or different embodiment of software application to associate the sequence information from each read with known haplotypes associated with tropism type, where the sequence data from the individual reads may or may not include variation from the consensus sequence. The term "haplotype" as used herein generally refers to the combination of alleles associated with a nucleic acid sequence, which in the case of HIV includes the HIV RNA sequence. Those of ordinary skill in the art will appreciate that the association may include the use of one or more specialized data structures, such as for instance one or more databases, which store haplotype and/or tropism association information. The software application may include or communicate with the data structures in known ways to extract information from and/or provide new information into the data structure.

Figures 4A, 4B:
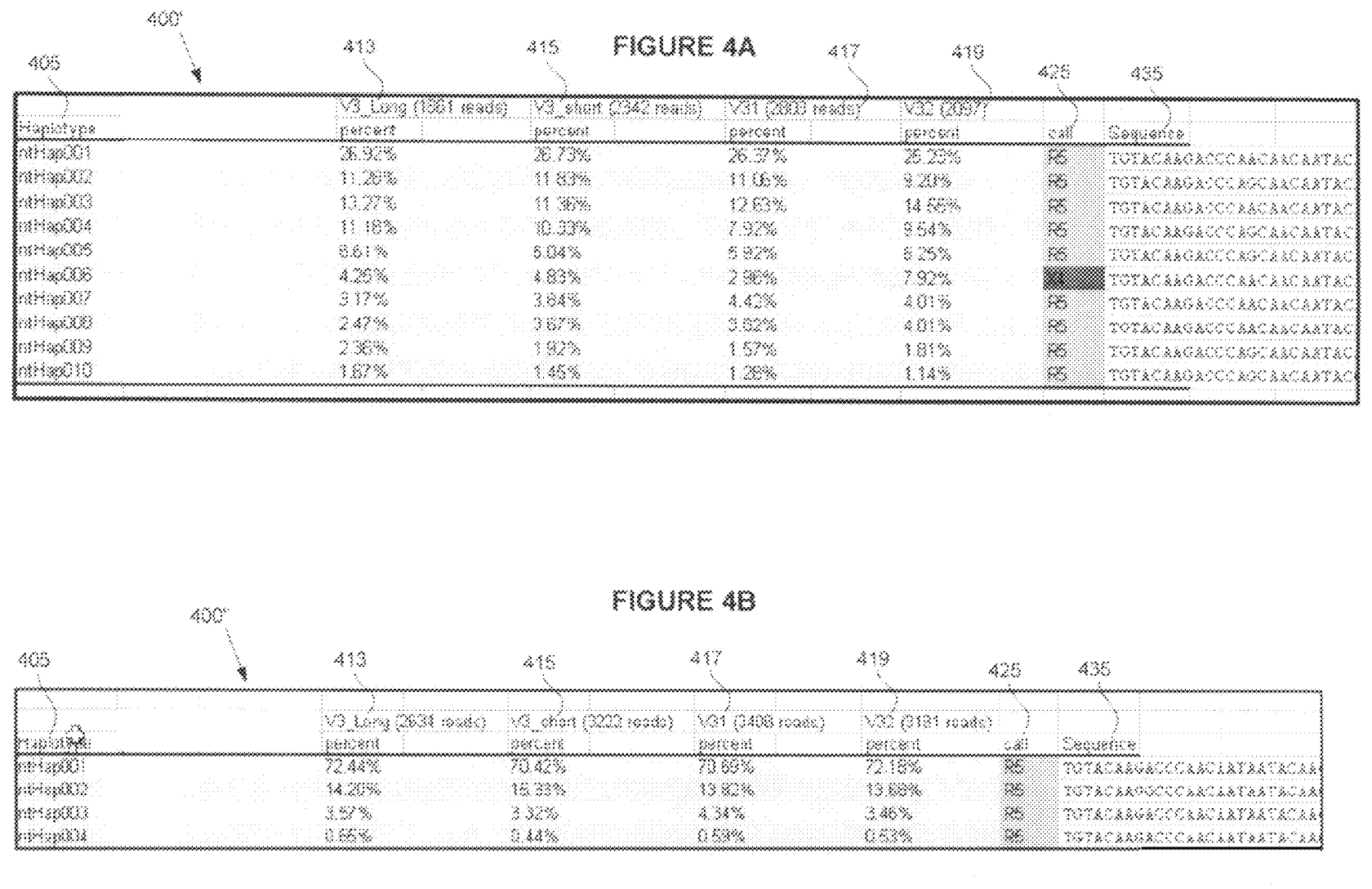

FIGS. 4A and 4B provide illustrative examples of the output of such sequence analysis software and includes interface 400' and 400'' respectively. Both examples 400' and 400'' illustrate identified haplotype 405; the frequency that the haplotype was identified in long amplicon 413, short amplicon 415, V3-1 amplicon 417, and V3-2 amplicon 419; tropism call 425, and haplotype sequence 435. Those of ordinary skill will appreciate that interface 400' provides a reference to "ntHap006" in haplotype 405 that corresponds to an X4 tropism type in tropism call 425. It will also be appreciated that interface 400'' provides a reference to "ntHap004" in haplotype 405 which was identified at less than a 1% frequency in each of amplicons 413, 415, 417, and 419.

As described above, sequencing many nucleic acid templates in parallel provides the sensitivity necessary for the presently described invention. For example, based on binomial statistics the lower limit of detection (i.e., one event) for a fully loaded 60 mm×60 mm PicoTiterPlate ($2 \times 10^6$ high quality bases, comprised of 200,000×100 base reads) with 95% confidence, is for a population with allelic frequency of at least 0.002%, and with 99% confidence for a population with allelic frequency of at least 0.003% (it will also be appreciated that a 70×75 mm PicoTiterPlate could be employed as described above, which allows for an even greater number of reads and thus increased sensitivity). For comparison, SNP detection via pyrophosphate based sequencing has reported detection of separate allelic states on a tetraploid genome, so long as the least frequent allele is present in 10% or more of the population (Rickert et al., 2002 BioTechniques. 32:592-603). Conventional fluorescent DNA sequencing is even less sensitive, experiencing trouble resolving 50/50 (i.e., 50%) heterozygote alleles (Ahmadian et al., 2000 Anal. BioChem. 280:103-110).

Table 1 shows the probability of detecting zero, or one or more, events, based on the incidence of SNP's in the total population, for a given number N (=100) of sequenced amplicons. "*" indicates a probability of 3.7% of failing to detect at least one event when the incidence is 5.0%; similarly, "**" reveals a probability of 0.6% of failing to detect one or more events when the incidence is 7%.

The table thus indicates that the confidence level to detect a SNP present at the 5% level is 95% or better and, similarly, the confidence of detecting a SNP present at the 7% level is 99% or better.

TABLE 1

| Incidence (%) | Prob. of at least 1 event (N = 100) | Prob. of no event (N = 100) |
|---|---|---|
| 1 | 0.264 | 0.736 |
| 2 | 0.597 | 0.403 |
| 3 | 0.805 | 0.195 |
| 4 | 0.913 | 0.087 |
| 5 | 0.963 | 0.037* |
| 6 | 0.985 | 0.015 |
| 7 | 0.994 | 0.006** |
| 8 | 0.998 | 0.002 |
| 9 | 0.999 | 0.001 |
| 10 | 1.000 | 0.000 |

Naturally, multiplex analysis is of greater applicability than depth of detection and Table 2 displays the number of SNPs that can be screened simultaneously on a single picotiter plate, with the minimum allelic frequencies detectable at 95% and 99% confidence.

TABLE 2

| SNP Classes | Number of Reads | Minimum frequency of SNP in population detectable with 95% confidence | Minimum frequency of SNP in population detectable with 99% confidence |
|---|---|---|---|
| 1 | 200000 | 0.002% | 0.003% |
| 2 | 100000 | 0.005% | 0.007% |
| 5 | 40000 | 0.014% | 0.018% |
| 10 | 20000 | 0.028% | 0.037% |
| 50 | 4000 | 0.14% | 0.18% |
| 100 | 2000 | 0.28% | 0.37% |
| 200 | 1000 | 0.55% | 0.74% |
| 500 | 400 | 1.39% | 1.85% |
| 1000 | 200 | 2.76% | 3.64% |

Figure 5:
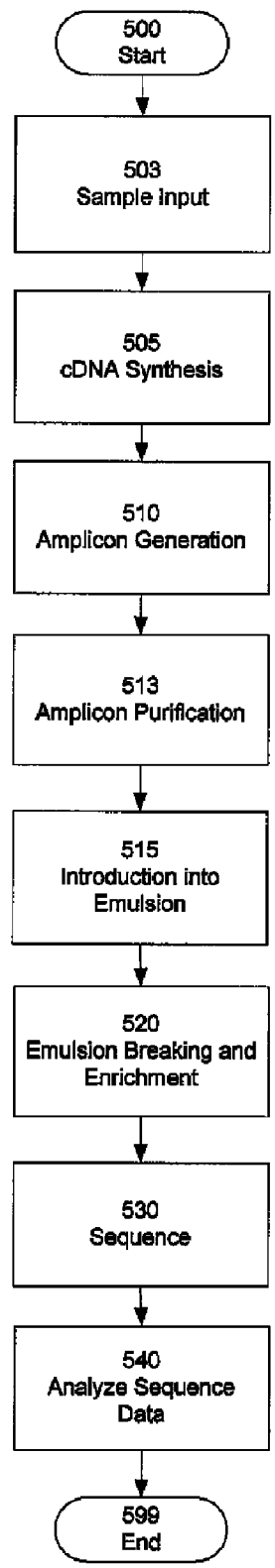
FIG. 5 is a functional block diagram of one embodiment of a method for identifying variation associated with HIV tropism.

FIG. 5 provides an illustrative example of one embodiment of a method for identification of low frequency variation in the HIV V3 region that includes step 503 for initial sample input. In order to consistently detect minor variants down to 3% frequency, HIV-1 RNA samples used for in the method require a minimum viral content of 160 IU/µl as determined with the Artus HIV real-time quantitative PCR assay (available from Artus Biotech GmbH). For detection down to 1% frequency, the minimum viral content should be at least 500 IU/µl.

If it is not practical to quantify the RNA samples, the RNA extraction can be performed on at least 140 µl of plasma into a total eluate of maximum 60 µl if the original viral load in the plasma is 100,000 copies per ml. For lower viral loads, scale the amount of plasma accordingly and pellet the virus for 1 hour 30 minutes at 20,600 rpm 4° C. Remove enough supernatant to leave 140 µl concentrate for the extraction procedure. Set up PCR and sequence duplicate reactions for several samples to verify consistent detection of low-frequency variants.

Next, the RNA sample is processed as illustrated in step 505 to generate one or more cDNA templates from an HIV sample population. Generating the cDNA from the sample may be performed using the following procedure:
1. Place 96 well plate in cooler
2. Add 11.5 µl RNA per well
3. Add 0.5 µl primer V3-1R

```
cDNA-V3-1R:
CATTACAATTTCTRGGTCYCCTCC      (SEQ ID NO: 2)
```

Incubate at 65° C. for 10 minutes then place tube immediately on ice.
Prepare the Reverse Transcriptase (RT) mix scaled up for number of tubes:
1. Transcriptor RT reaction buffer (available from Roche) 4 µl
2. Protector RNase Inhibitor (available from Roche) 0.5 µl
3. dNTPs 2 µl
4. DTT (available from Roche) 1 µl
5. Transcriptor Reverse Transcriptase (available from Roche) 0.5 µl Mix briefly by vortexing and keep on ice until added to the RNA sample.
6. Add 8 µl RT mix per well
7. Seal plate and centrifuge briefly
8. Place in thermocycler and run the following cDNA program
   60 min, 50° C.
   5 min, 85° C.
   4° C. forever
9. Add 1 µl RNAse H (available from New England Biolabs) per well
10. Place in thermocycler block at 37° C. (with heated lid set at or above 50° C.) for 20 min.
11. Proceed immediately to amplicon generation or store the cDNA at −80° C.

Subsequently, as illustrated in step 510, pairs of region specific primers are employed to amplify target region from the cDNA templates generated in step 505 using the following procedure.
1. The 13× mix described below is sufficient for one 96 well plate (2 amplicons, 47 samples +1 control). The method can be scaled up or down as necessary.
2. Label 2 1.5 ml centrifuge tubes "V3-1", and "V3-S". These labels refer to the following amplicons/primer sets:
   V3-1 V3-1F+V3-1R
   V3-S V3-2F+V3-1R
   (Note: in addition to the target specific primer sequences described above, the following primers include the following elements: +6 bases, forward=CGTATC, reverse=CTATGC; SAD sequence specific for forward and reverse primers; and Key element=TCAG)

```
V3-1F                                       (SEQ ID NO: 5)
CGTATCGCCTCCCTCGCGCCATCAGTCAGCACAGTACARTGYACACATGG

V3-1R                                       (SEQ ID NO: 6)
CTATGCGCCTTGCCAGCCCGCTCAGCATTACAATTTCTRGGTCYCCTCC

V3-2F                                       (SEQ ID NO: 7)
CGTATCGCCTCCCTCGCGCCATCAGCAACTCAACTRCTGTTAAATGGYAG
```

3. If Multiplex Identifiers (MIDs) are required for the experiment, then for each set of amplicons add in the corresponding MID primer. E.g. if using MID1, then all primers of primer set A should have MID1 added into the primer for both the forward and reverse directions. MID sequence is 10 base pairs long and should be inserted into the primer following the sequence adaptor sequence and immediately prior to the target primer sequence.

4. In each tube, prepare a PCR master mix with the primer set indicated by the label:

|  | 1x mix | 13x mix |
|---|---|---|
| Forward primer | 1 µl | 13 µl |
| Reverse primer | 1 µl | 13 µl |
| dNTP mix | 0.5 µl | 6.5 µl |
| FastStart 10x buffer #2 | 2.5 µl | 32.5 µl |
| FastStart Hifi polymerase | 0.25 µl | 3.25 µl |
| molecular grade water | 16.75 µl | 217.75 µl |
| total volume | 22 µl | 286 µl |

5. Pipet 22 µl "V3-1" PCR master mix into each well in first row.
6. Pipet 22 µl "V3-S" PCR master mix into each well in second row.
7. Add 3 µl cDNA per well according to the following scheme (one sample per column)
8. The positive control in column 11 is the known sample cDNA and the negative control in column 12 is the water control from the cDNA synthesis plate.
9. Cover the plate with a plate seal.
10. Centrifuge the plate 30 sec at 900×g.
11. Place the plate in a thermocycler block and run the program "Ti_V3 Amp"
    94° C. 3 min
    40 cycles:
      94° C. 15 sec
      55° C. 20 sec
      72° C. 45 sec
    72° C. 8 min
    4° C. forever
12. If not proceeding with the next step immediately, store the plate on ice (for processing the same day) or at −20° C.

The amplicons generated in step 510 may then, in some embodiments, be cleaned up or purified as illustrated in step 513 using either Solid Phase Reversible Immobilization (also referred to as SPR1) or gel cutting methods for size selection known in the related art. For instance, amplicon purification may be performed using the following process:

1. Centrifuge the plate for 30 sec at 900×g.
2. Using an 8-channel multipipettor, pipet 22.5 µA molecular grade water into each well in columns 1-11 of a 96-well, round bottom, PP plate (available from Fisher Scientific).
3. Transfer 22.5 µl PCR product from the PCR plate to each well of the round bottom PP plate; keep the layout the same for the two plates.
4. Add 72 µl SPR1 beads to each well and mix thoroughly by pipetting up and down at least 12 times until the SPR1 bead/PCR mixture is homogeneous.
5. Incubate the plate 10 min at room temperature until supernatant is clear.
6. Place the plate on a 96-well magnetic ring stand (available from Ambion, Inc.) and incubate for 5 min at room temperature.
7. With the plate still on the magnetic ring stand, carefully remove and discard the supernatant without disturbing the beads.
8. Remove the PP plate from the magnetic ring stand and add 200 µl of freshly prepared 70% ethanol.
9. Return the PP plate to the magnetic ring stand. Tap or move the PP plate in a back and forth/circular motion over the magnetic ring stand ~10 times to agitate the solution and assist in pellet dispersion (the pellet may not fully disperse; this is acceptable).
10. Place the PP plate on the magnetic ring stand and incubate 1 min.
11. With the plate still on the magnetic ring stand, carefully remove and discard the supernatant without disturbing the beads.
12. Repeat steps 8-11. Remove as much of the supernatant as possible.
13. Place the PP plate/magnetic ring stand together on a heat block set at 40° C. until all pellets are completely dry (10-20 min.)
14. Add 10 µl 1×TE (pH 7.6±0.1) to each well. Tap/move the PP plate in the same back and forth/circular motion over the magnetic ring stand until all pellets are dispersed.
15. Place the PP plate on the magnetic ring stand and incubate for 2 min.
16. Pipet the supernatant from each well into a fresh 96-well (yellow) plate. It is difficult to avoid any transfer of pellet in some of the wells; this is acceptable.
17. Cover the plate with a plate seal and store at −20° C.

In the one or more embodiments, it may also be advantageous to quantitated the amplicons. In the present example, amplicon quantitation may be performed using the following process:

1. Using methods known in the art quantify 1 µl of these amplicons with PicoGreen® reagent.
2. Any amplicon quantified at or below 5 ng/µl should be further evaluated on the 2100 Bioanalyzer (available from Agilent Technologies): Load 1 µl of each purified amplicon on a Bioanalyzer DNA chip and run the DNA-1000 series II assay.
   a. If a band of the expected size is present and primer dimers are evident at a molar ratio of 3:1 or less, use the PicoGreen quantification and proceed with amplicon pooling.
   b. If a band of the expected size is present and primer dimers are evident at a molar ratio above 3:1, repeat SPR1 and PicoGreen quantitation, followed by Bioanalyzer analysis to confirm removal of primer dimers.
3. Analyze 1 µl of the negative PCR control reactions on the Bioanalyzer. No bands other than primer dimers should be visible Next, as illustrated in step 515 nucleic acid strands from the amplicons are selected and introduced into emulsion droplets and amplified as described elsewhere in this specification. In some embodiments, two emulsions may be set up per sample, one using an Amplicon A kit and one using an Amplicon B kit both available from 454 Life Sciences Corporation. It will be appreciated that in different embodiments, different numbers of emulsions and/or different kits can be employed. Amplicons may be selected for the final mix using the following process:

1. 2 amplicons for each sample are generated, each of which ideally should be mixed in equimolar amounts for the emPCR reaction. As not all amplicons are generated with equal efficiency and occasionally there is very little amplicon made but a large amount of primer dimers may be present instead. To achieve optimal sequencing results it is important to only use well-quantified and relatively pure (see below) amplicons for the final mix for each sample even when the quality of some amplicons is substandard. Due to the considerable overlap between the various amplicons, this is possible as not all 2 amplicons are needed for complete coverage of a given sample. When the set of 2 high quality amplicons is not available follow the rules below for choosing amplicons for the final mix for each sample:
  i. If the amplicon is not recognized as a quantifiable band on the Bioanalyzer, do not use it for the final amplicon mix in 6.2.
  ii. If the molar ratio of primer-dimer to amplicon is 3:1 or more, do not use for the final amplicon mix. This measurement will only be available for the low-concentration amplicons that were further quantified with the Agilent Bioanalyzer assay in 6.1.
  iii. If an amplicon fails the above criteria or is altogether missing, increase the amount of the other overlapping amplicon according to the following scheme:
2. If amplicon V3-1 is missing, double the amount of amplicon V3-S.
3. If amplicon V3-S is missing, double the amount of amplicon V3-1.
4. If both amplicons V3-1 and V3-S are missing, the V3 region cannot be sequenced. Repeat PCR for these amplicons.

Also as part of step 515 the following process for mixing and dilution of the amplicons may be employed for use in emPCR:
1. Calculate the concentration in molecules per μl for each of the 2 amplicons derived from a given sample using the following equation:

$$\text{Molecules}/\mu l = \frac{\text{sample conc [ng/}\mu\text{l]} * 6.022 * 10^{23}}{656.6 * 10^9 * \text{amplicon length [bp]}}$$

2. Make a $10^9$ molecules/μl dilution of each of the 2 amplicons:
  To 1 μl of amplicon solution add the following volume of 1×TE:

$$\left(\frac{\text{molecules}/\mu l \text{ (from 6.3.1)}}{10^9} - 1\right)\mu l$$

3. Mix an equal volume of each of the 2 amplicon dilutions, e.g., 10 μl. If either of the amplicons are missing, increase the volumes of overlapping amplicons according to the guidelines in step 505.
4. Make a further dilution of the mixed amplicons to $2\times10^6$ molecules/μl by adding 1 μl of the $10^9$ molecules/μl solution to 499 μl 1×TE
5. Store the final dilution ($2\times10^6$ molecules/μl) at $-20°$ C. in a 0.5 ml tube with o-ring cap.

After the amplification the emulsions are broken and beads with amplified populations of immobilized nucleic acids are enriched as illustrated in step 520. For example, DNA-containing beads may be enriched as described elsewhere in this specification, which may include the following process elements:
1. Immediately before setting up emulsions, make a 10-fold dilution of the $2\times10^6$ molecules/μl solution from 6.3.4 by adding 10 μl to 90 μl bead wash buffer. Vortex 5 sec. to mix.
2. For each sample, make one A and one B emulsion with 1 cpb (i.e., 12 μl of the above dilution per emulsion (2,400,000 beads)).
3. The two emulsions for a given sample can be pooled during breaking for easier handling.

The enriched beads are then sequenced as illustrated in step 530. In some embodiments, each sample is sequenced as described elsewhere in this specification. For instance, after enrichment and processing for sequencing, load 80,000 beads (including the positive control sample) from the combined emulsions per lane on a 70×75 metallized PTP fitted with a 16-lane gasket and sequence on a GS-FLX instrument (available from 454 Life Sciences Corporation).

The GS-FLX sequencing instrument comprises three major assemblies: a fluidics subsystem, a fiber optic slide cartridge/flow chamber, and an imaging subsystem. Reagents inlet lines, a multi-valve manifold, and a peristaltic pump form part of the fluidics subsystem. The individual reagents are connected to the appropriate reagent inlet lines, which allows for reagent delivery into the flow chamber, one reagent at a time, at a pre-programmed flow rate and duration. The fiber optic slide cartridge/flow chamber has a 250 μM space between the slide's etched side and the flow chamber ceiling. The flow chamber also included means for temperature control of the reagents and fiber optic slide, as well as a light-tight housing. The polished (unetched) side of the slide is placed directly in contact with the imaging system.

The cyclical delivery of sequencing reagents into the fiber optic slide wells and washing of the sequencing reaction byproducts from the wells is achieved by a pre-programmed operation of the fluidics system. The program is typically written in a form of an Interface Control Language (ICL) script, specifying the reagent name (Wash, dATPaS, dCTP, dGTP, dTTP, and PPi standard), flow rate and duration of each script step. For example, in one possible embodiment flow rate can be set at 4 mL/min for all reagents with the linear velocity within the flow chamber of approximately ~1 cm/s. The flow order of the sequencing reagents may be organized into kernels where the first kernel comprises of a PPi flow (21 seconds), followed by 14 seconds of substrate flow, 28 seconds of apyrase wash and 21 seconds of substrate flow. The first PPi flow may be followed by 21 cycles of dNTP flows (dC-substrate-apyrase wash-substrate dA-substrate-apyrase wash-substrate-dG-substrate-apyrase wash-substrate-dT-substrate-apyrase wash-substrate), where each dNTP flow is composed of 4 individual kernels. Each kernel is 84 seconds long (dNTP-21 seconds, substrate flow-14 seconds, apyrase wash-28 seconds, substrate flow-21 seconds); an image is captured after 21 seconds and after 63 seconds. After 21 cycles of dNTP flow, a PPi kernel is introduced, and then followed by another 21 cycles of dNTP flow. The end of the sequencing run is followed by a third PPi kernel. The total run time was 244 minutes. Reagent volumes required to complete this run are as follows: 500 mL of each wash solution, 100 mL of each nucleotide solution. During the run, all reagents were kept at room temperature. The temperature of the flow chamber and flow chamber inlet tubing is controlled at 30° C. and all reagents entering the flow chamber are pre-heated to 30° C.

Subsequently, the output sequence data is analyzed as illustrated in step 540. In some embodiments, SFF files containing flow gram data filtered for high quality are processed using specific amplicon software and the data analyzed.

It will be understood that the steps described above are for the purposes of illustration only and are not intended to be limiting, and further that some or all of the steps may be employed in different embodiments in various combinations.

For example, the primers employed in the method described above may be combined with additional primers sets for interrogating other HIV characteristics/regions to provide a more comprehensive diagnostic or therapeutic benefit. In the present example, such combination could be provided "dried down" on a plate and include the described tropism primers as well as some or all of the primers for detection of HIV drug resistance or the Integrase region, as well as any other region of interest. Additional examples are disclosed in PCT Application Serial No US 2008/003424, titled "System and Method for Detection of HIV Drug Resistant Variants", filed Mar. 14, 2008; and/or U.S. Provisional Patent Application Ser. No. 61/118,815, titled "System and Method for Detection of HIV Integrase Variants", filed Dec. 1, 2008, each of which is hereby incorporated by reference herein in its entirety for all purposes.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

What is claimed is:

1. A nucleic acid sequencing kit for detecting a low frequency occurrence of one or more HIV Tropism sequence variants, comprising:
a plurality of nucleic acid primers adapted to clonally amplify by PCR and sequence an HIV V3 region from a plurality of HIV clades comprising clade A, clade B, clade C, clade D, and clade G, wherein the nucleic acid primers comprise a V3-1F primer (SEQ ID NO: 5); a and V3-1R primer (SEQ ID NO: 6); and a V3-2F primer (SEQ ID NO: 7).

2. The kit of claim 1, further comprising: a V3-1R primer (SEQ ID NO: 2) adapted to amplify a plurality of cDNA species from a plurality of RNA molecules in an HIV sample population derived from a single patient.

3. The method of claim 2, wherein:
the plurality of cDNA species have overlapping sequence composition.

4. The kit of claim 1, wherein:
the plurality of primers target regions of low mutation frequency.

5. The kit of claim 1, wherein:
the plurality of nucleic acid primers comprise pairs adapted to target a locus comprising the V3 region of HIV.

6. The kit of claim 4, wherein:
the V3 region is associated with an HIV envelope region.

7. The kit of claim 1, further comprising:
a single substrate comprising a plurality of reaction sites.

8. The kit of claim 1 wherein:
the plurality of HIV clades further comprise clade F, clade H, clade J, and clade K.

* * * * *

UNITED STATES PATENT AND TRADEMARK OFFICE
CERTIFICATE OF CORRECTION

PATENT NO. : 8,344,123 B2
APPLICATION NO. : 12/970036
DATED : January 1, 2013
INVENTOR(S) : Birgitte B. Simen It is certified that error appears in the above-identified patent and that said Letters Patent is hereby corrected as shown below:

In Column 31, Claim 1, line 55, delete the word "and".

Signed and Sealed this
Nineteenth Day of February, 2013

Teresa Stanek Rea
*Acting Director of the United States Patent and Trademark Office*